US011680287B2

(12) United States Patent
Snaidr et al.

(10) Patent No.: US 11,680,287 B2
(45) Date of Patent: Jun. 20, 2023

(54) METHOD FOR THE SPECIFIC DETECTION OF MICROORGANISMS

(71) Applicant: VERMICON AG, Munich (DE)

(72) Inventors: Jiri Snaidr, Munich (DE); Claudia Beimfohr, Munich (DE); Peter Muhlhahn, Munich (DE)

(73) Assignee: Vermicon AG, Munich (DE)

( * ) Notice: Subject to any disclaimer, the term of this patent is extended or adjusted under 35 U.S.C. 154(b) by 497 days.

(21) Appl. No.: 16/641,308

(22) PCT Filed: Aug. 16, 2018

(86) PCT No.: PCT/EP2018/072240
§ 371 (c)(1),
(2) Date: Mar. 26, 2020

(87) PCT Pub. No.: WO2019/038181
PCT Pub. Date: Feb. 28, 2019

(65) Prior Publication Data
US 2020/0385793 A1 Dec. 10, 2020

(30) Foreign Application Priority Data
Aug. 22, 2017 (EP) .................... 17187339

(51) Int. Cl.
*C12Q 1/68* (2018.01)
*C12Q 1/6841* (2018.01)
*G01N 15/14* (2006.01)
(52) U.S. Cl.
CPC .......... *C12Q 1/6841* (2013.01); *G01N 15/14* (2013.01); *C12Q 2563/107* (2013.01)

(58) Field of Classification Search
CPC . C12Q 1/6841; C12Q 2563/107; G01N 15/14
See application file for complete search history.

(56) References Cited

U.S. PATENT DOCUMENTS

2005/0136446 A1\* 6/2005 Snaidr .................. C12Q 1/6841
435/6.11

FOREIGN PATENT DOCUMENTS

| DE | 102010/012421 | 9/2010 |
| JP | H0746101 B2 \* | 5/1995 |
| WO | WO 03/083131 A1 | 10/2003 |
| WO | WO 16/178953 A1 | 11/2016 |

OTHER PUBLICATIONS

International Search Report, dated Sep. 6, 2018 for International Application No. PCT/EP2018/072240, 6 pages.
Morrison et al., Solution-Phase Detection of Polynucleotides Using Interacting Fluorescent Labels & Competitive Hybridization, Analytical Biochemistry 183, 231-244 (1989).
Shepherd et al., Counting Small RNA in Pathogenic Bacteria, Analytical Chemistry, Apr. 25, 2013, pp. 4938-4943.
Hye Yoon Park et al., "Tracking Single MRNA Molecules in Live Cells", Methods in Enzymology vol. 472, 2010, pp. 387-408.

\* cited by examiner

*Primary Examiner* — Jezia Riley
(74) *Attorney, Agent, or Firm* — Watts Law LLC; Samantha R. Smart

(57) ABSTRACT

The invention relates to a method for the specific detection of a microorganism or a group of microorganisms via in situ hybridisation by means of flow cytometry.

19 Claims, 5 Drawing Sheets

METHOD FOR THE SPECIFIC DETECTION OF MICROORGANISMS

CROSS-REFERENCES TO RELATED APPLICATIONS

The present application is a 35 U.S.C. § 371 National Stage Patent Application of International PCT Application Serial No. PCT/EP2018/072240 having an International filing date of 16 Aug. 2018 and that was published on 28 Feb. 2019 under international publication number WO 2019/038181, which claims priority to German Patent Application No. 17187339.1 filed 22 Aug. 2017. This Application claims priority to and incorporates by reference the above-identified applications and publication in their entireties for all purposes.

The present invention relates to a method for the specific detection of microorganisms or a group of microorganisms through in situ hybridization by means of flow-through cytometry.

Microbial routine analysis in the food industry is confronted in many fields with a high sampling rate (>100 samples per day), which have to be quickly processed as simultaneously as possible. There are systems with automatic evaluation and objective result determination for processing such a high throughput with a specific, molecular biological, fast detection system.

The so-called fluorescence in situ hybridization (FISH) has become established as a modern method for determining bacteria that can fulfill these requirements, in the original embodiment of which, cells are made visible under a microscope on an object carrier through fluorescence marked nucleic acid probe molecules (Amann et al., Microbial. Rev. 59 (1995), 143-169). The classic FISH technology has the problem, however, that the detection by means of a microscope requires well instructed laboratory personnel and a considerable amount of time, which naturally severely limits the number of samples that can be analyzed per day.

In order to resolve this problem, a fluorescence in situ hybridization in the liquid phase based on the reaction mechanism of the classic FISH technology has been proposed since then, in which all of the steps of the hybridization reaction are transferred nearly unchanged from the object carrier format to the reaction vessel format, and a detection by means of a flow-through cytometer takes place (WO 03/083131 A1). The various hybridization and rinsing solutions were removed in this method via centrifugation.

In particular, the necessary rinsing steps in the whole cell hybridization for increasing the sound/noise ratio in the routine analysis require a lot of work and also require well instructed laboratory personnel. Furthermore, the necessary steps for removing the aqueous residue in the centrifugation represents a further processing parameter that must be taken into account in assessing the observed results and the necessary standardization of the method.

DE 10 2010 012 421 A1 discloses a method for the specific detection of microorganisms that can be carried out quickly and does not require the necessary rinsing steps in the classic FISH technology. In detail, the method comprises an execution of the hybridization reaction in a microtiter plate and the subsequent determination of the results via a microtiter plate reader, wherein the output fluorescence signal corresponds to the sum of the fluorescence marked nucleic acid probes specifically bonded to the microorganisms.

A significant prerequisite for this semi-quantitative bacteria detection is the specific fluorescence quenching of un-bonded fluorescence marked nucleic acid probe molecules within the reaction space on the microtiter plate, in order to discriminate between specific and unspecific signals. The method has the disadvantage that there is no precise quantification of the number of cells, because the number of specific bonded fluorescence marked nucleic acid probe molecules per cell (and thus the contribution of a cell to the measured fluorescence signal strength) cannot be determined clearly. A single cell can normally bond with between 5,000 and 15,000 fluorescence marked oligonucleotide probes.

The fundamental object of the invention is therefore to create a method for detecting microorganisms in general, and specific microorganisms, that overcomes the aforementioned disadvantages of the prior art. In particular, the method should be as simple as possible (i.e. with as little technological complexity and without highly trained laboratory personnel), and it should offer the possibility of analyzing a large number of samples in a short time, while simultaneously ensuring a high level of specificity for microorganisms relevant to the samples. This determination and analysis of the results should be objective and standardized.

According to the invention, this problem is solved by a method defined in claim 1. The method according to the invention enables a quick and specific detection of microorganisms without requiring a rinsing step such as that required in the classic FISH technology. In addition, the non-specific autofluorescence occurring in the FISH technology, and in particular in the classic FISH technology, that may be problematic for the evaluation, is suppressed.

Furthermore, the method according to the invention is substantially simplified compared to the microtiter plate method described in DE 10 2010 012 421 A1, in that the conventional method steps are shortened to the addition of two reaction solutions to the samples, and the reaction can take place in a single reaction vessel. In addition, it is possible to directly quantify the number of detected microorganisms through the use of a flow-through cytometer in the detection.

Lastly, the present method can at least be automated with regard to its execution and evaluation. The method according to the invention is consequently suitable in particular for an analysis with a high throughput as well.

BRIEF DESCRIPTION OF THE DRAWINGS

The foregoing and other features and advantages of the present disclosure will become apparent to one skilled in the art to which the present disclosure relates upon consideration of the following description of the disclosure with reference to the accompanying drawings, wherein like reference numerals, unless otherwise described refer to like parts throughout the drawings and in which.

Figure 1:
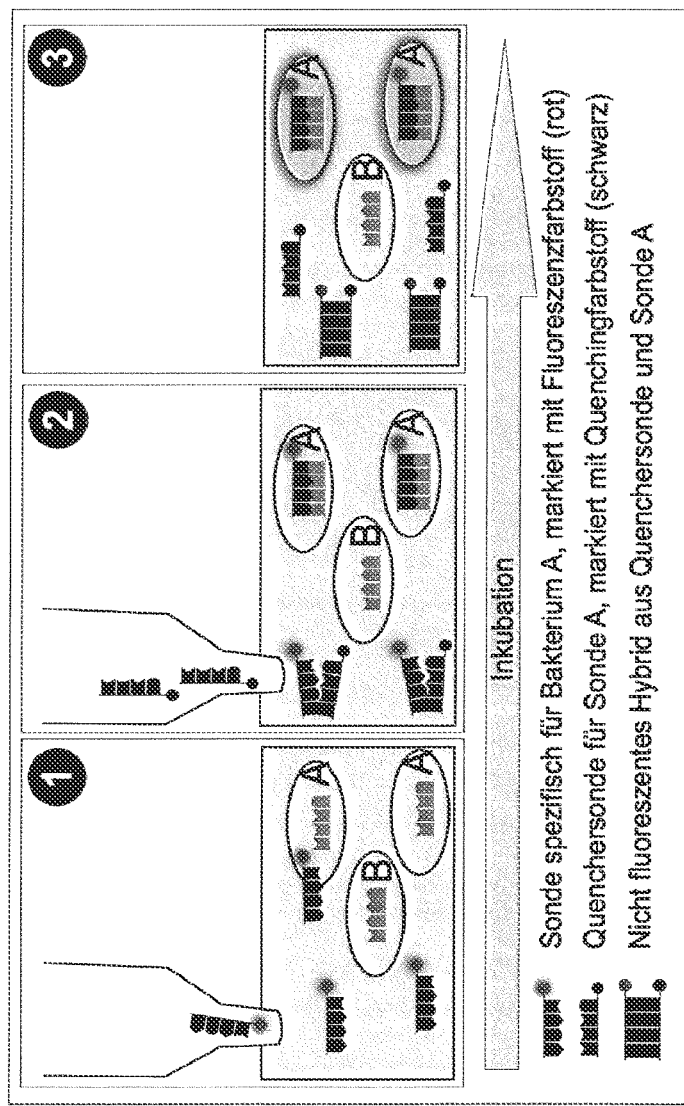
FIG. 1 schematically illustrates the reactions in the method that is the basis for the invention, wherein both the fluorescence-marked nucleic acid probes as well as the quencher-marked nucleic acid probes are present in the concrete example as single-stranded DNA molecules.

The execution of the method according to the invention for the specific detection of a microorganism or numerous microorganisms in a sample comprises the following steps:

(a) obtaining the sample;

(b) fixing the cells contained in the sample in place with a fixing agent, and separating the fixed cells obtained thereby from the sample, in order to obtain fixed cells;

(c) bringing the fixed cells in contact with a chemical homogenizing agent and drying the homogenized cells obtained thereby, in order to obtain dried cells;

(d) bringing the dried cells in contact with a solution of a fluorescence marked nucleic acid probe specific for the microorganism that is to be detected, in order to obtain a first reaction mixture;

(e) incubating the first reaction mixture in order to bond the fluorescence marked nucleic acid probe to the corresponding target nucleic acid sequence in the cells of the microorganism that is to be detected;

(f) bringing the first reaction mixture in contact with a solution of a quencher-marked nucleic acid probe, following step (e), in order to obtain a second reaction mixture, wherein the quencher-marked nucleic acid probe comprises a quencher that at least partially quenches the fluorescence of the fluorescence-marked nucleic acid probe, and contains a nucleic acid sequence that is substantially complementary to the nucleic acid sequence of the fluorescence-marked nucleic acid probe;

(g) incubating the second reaction mixture to cause a bonding of the molecules of the fluorescence-marked nucleic acid probe not bonded to the target nucleic acid sequence in the cells of the microorganism that is to be detected to the quencher-marked nucleic acid probe; and (h) placing the second reaction mixture in a flow-through cytometer after step (g), and detecting the fluorescence emitted from the cells of the microorganism that is to be detected containing the fluorescence-marked nucleic acid probe.

The present invention relates to the specific detection of a single microorganism or numerous (i.e. at least two different) microorganisms in a naturally or synthetically occurring sample. It should be understood that when detecting such a microorganism in the method according to the invention, more than just one single cell is detected. Normally one or more cells are detected, wherein the detection is based on the detection of the fluorescence emitted from a single cell.

The term, "microorganism," as it is used in the present application comprises both naturally occurring as well as synthetically generated microorganisms that can be of a pathogenic or non-pathogenic nature, and contain, among other things, bacteria, fungi, microalgae, and protozoa. The at least one microorganism that is to be detected is preferably a bacteria, a fungi, or a single-cell higher organism (protozoa), wherein the bacteria, fungi, and/or single-cell higher organism can come from an arbitrary taxonomic unit, and the term, "taxonomic unit," comprises, among other things, domains/kingdoms, divisions/phyla, classes, sub-classes, orders, suborders, families, subfamilies, genuses, sub-genuses, types, sub-types, strains, and sub-strains.

Concrete examples of microorganisms that can be detected by means of the method according to the invention comprise, in particular, bacteria, fungi (comprising yeasts and molds) and protozoa, which are known to compromise the quality of water (including waste water), beverages (e.g. water, beer, fruit juices and non-alcohol refreshment beverages) and food (e.g. milk products such as cheese and yogurt, as well as meet products such as sausages), and are named in DE 101 29 410 A1, DE 101 60 666 A1 and WO 2005/031004 A2, among others. The detection of bacteria, yeasts and molds is particularly preferred in this context.

Bacteria relevant to the sample are, in particular, bacteria of the genus *Acetobacter, Achromobacter, Acinetobacter, Aerococcus, Aeromonas, Agrobacteria, Alcaligenes, Alicyclobacillus, Aneurinibacillus, Anoxybacillus, Aquabacteria, Arcobacter, Arthrobacter, Arthrobacter, Bacillus, Brevibacillus, Brevibacterium, Brocardia, Brochothrix, Burkholderia, Caldanaerobius, Campylobacter, Carnobacterium, Cellulomonas, Chloroflexi, Chryseobacterium, Chryseobacterium, Citrobacter, Cloacibacterium, Clostridium, Colwellia, Corynebacterium, Cronobacter, Delftia, Desulfotomaculum, Dickeya, Enterobacter, Enterobacteriaceae, Enterococcus, Erwinia, Escherichia, Facklamia, Flavobacteriaceae, Flavobacterium, Fructobacillus, Geobacillus, Gluconacetobacter, Gluconobacter, Janthinobacterium, Jeotgalibacillus, Kocuria, Komagtaeibacter, Kuenenia, Kurthia, Lactobacillus, Lactococcus, Legionella, Lentibacillus, Leuconostoc, Listeria, Lysinibacillus, Macrococcus, Marinilactibacillus, Megasphaera, Microbacterium, Micrococcus, Microthrix*, Lactic acid bacteria, *Moorella, Moraxella, Nitrobacter, Nitrosococcus, Nitrosomonas, Nitrospira, Nitrotoga, Nocardia, Nostocoida, Obesumbacterium, Oceanobacillus, Oenococcus, Paenibacillus, Pantoea, Pectinatus, Pectobacterium, Pediococcus, Pedobacter, Photobacterium, Prevotella, Propionibacterium, Pseudoalteromonas, Pseudomonas, Psychrobacillus, Psychrobacter, Psychroflexus, Rhizobium, Salmonella, Scalindua, Serratia, Shewanella, Shigella, Solibacillus, Sphingobacterium, Sphingomonas, Sporolactobacillus, Sporosarcina, Staphylococcus, Stenotrophomonas, Streptococcus, Streptomyces, Tepidomonas, Thermoanaerobacterium, thermophilic bacteria, Thiothrix, Trichococcus, Ureibacillus, Vagococcus, Vibrio, Virgibacillus, Viridibacillus, Weissella, Xanthomonas, Yersinia*, and *Zymomonas*.

Fungi relevant to the samples that could be detected by means of the method of the present invention comprise, in particular, molds and yeasts of the genuses *Aspergillus, Candida, Debaromyces, Dekkera, Geotrichum, Hanseniaspora, Hyphopichia, Kazachstania, Kloeckera, Kluyveromyces, Lodderomyces, Penicillium, Pichia, Rhodotorula, Saccharomyces, Saccharomycopsis, Schizosaccharomyces, Torulaspora, Wickerhamomyces, Yarrowia*, and *Zygosaccharomyces*.

Single-cell higher organisms (protozoa) relevant to the sample that could be detected by means of the method of the present invention comprise, in particular, *Giardia, Cryptosporidium, Amoeba, Trichomonas, Toxoplasma, Balantidium*, and *Blastocystis*.

Regarding the detection of microorganisms in water, beverages and food, bacteria of the genuses *Acinetobacter, Alicyclobacillus, Aquabacterium, Arcobacter, Bacillus, Campylobacter, Enterobacteriaceae, Escherichia, Lactobacillus, Lactococcus, Legionella, Listeria, Microthrix, Nitrobacter, Nitrosococcus, Nitrosomonas, Nitrospira, Nitrotoga, Propionibacterium, Salmonella, Shigella* and *Streptococcus*, as well as fungi of the genuses *Aspergillus, Candida, Debaromyces, Dekkera, Penicillium, Pichia* and *Sccharomyces* are of particular relevance, for which reason the detection thereof is regarded as particularly preferable.

The sample, as it is used in the method according to the invention, is preferably a liquid sample. It is sufficient when at least a portion of the individual cells of the microorganism that is to be detected are present in the liquid phase. In this regard, a just partially liquid sample, or a suspension or dispersion can also be used according to the invention, although a solution is preferred. An aqueous sample is particularly preferably used as the liquid sample, e.g. a water sample or a beverage sample that as such is subjected to analysis (i.e. without adding further liquid).

The sample that is to be analyzed in the framework of executing the method according to the invention can be any primary sample from which a secondary sample is generated, which is then used as the liquid sample in method according to the invention. A primary sample can be a solid, paste-like, liquid, or gaseous sample. A representative mixture of microorganisms is typically obtained from the primary sample, which is then converted into the liquid sample, as it is used in the method according to the invention.

After a sample has been obtained for analysis, the cells of the microorganism or microorganisms contained in the sample are fixed in place in the method according to the invention using a fixing agent. The term, "fixing," as it is used in the present application, is well known in the field of cell biology, and refers in general to a preservation of biological samples for subsequent studies. A method for fixing cells in place that can be used in FISH technologies is described, for example, in Amann et al. (Nature Reviews Microbiology 6 (2008), 339-350).

Because of the diversity of the cell envelope systems and in particular the cell walls of the various microorganisms that are to be detected, the reaction conditions for the fixing are preferably adapted to the respective microorganism that is to be detected. In the present invention, an alcohol, in particular a short chain alcohol, such as methanol, ethanol, or isopropanol, or an aldehyde, in particular a short chain aldehyde, such as formaldehyde or paraformaldehyde, is used as the fixing agent. The precise reaction conditions of a fixing procedure using such a fixing agent can be determined by a person skilled in the art in the field of microbial diagnostics through simple standard tests and routine experiments.

The fixing of the cells contained in the sample takes place according to the invention before the cells are brought in contact with the detection reagent specific for the respective microorganism. This involves maintaining both the integrity as well as, to a certain extent, the shape of the cells that are to be detected, as well preventing a loss of cells in the microorganism that is to be detected, in particular through lysis. On the other hand, it is important to make as many cells of the microorganism that is to be detected as possible permeable through the fixing, such that the nucleic acid probes contained in the detection reagent can preferably permeate the cells individually, or as a single strain, in order to therein hybridize with the target sequence(s), if present.

In addition to the treatment with the fixing agent, the step of fixing the cells can also comprise an enzymatic treatment of the cells or cell envelope system, which may be of particular interest with gram-positive bacteria, yeasts or molds. In order to increase the permeability of the cell wall for the specific detection reagent added later, a modification of the peptidoglycan shell by means of lysozyme can take place in the case of gram-positive bacteria, for example, or a modification of the protein cell wall by means of proteases can be carried out in the cases of yeasts and molds, for example.

Further treatments can comprise the brief treatment of the cells with solvents or hydrochloric acid to remove waxy layers or the like. In a preferred embodiment of the method according to the invention, the fixing step for the cells results in the fixed cells no longer being capable of life, but nevertheless remaining intact, preferably morphologically intact.

After the cells have been fixed with a suitable fixing agent, and have been optionally further treated with an enzyme or the like, the fixed cells are removed from the sample. For this, the sample is advantageously centrifuged, upon which the sedimented cells are subjected to further processing, and the excess is discarded. Other methods for separating the fixed cells from the sample are well known to the person skilled in the art in the field of microbial diagnostics, and can be used according to circumstances in the appropriate manner.

In order to enable a quantification of individual cells in a flow-through cytometer it is necessary in the method according to the invention that a chemical homogenizing agent is added to the fixed cells prior to bringing them in contact with the detection reagent specific for the respective microorganism that is to be detected, and subsequently dried. The term, "chemical homogenizing agent," as it is used herein refers to a chemical reagent that prevents the aggregation of fixed cells during the subsequent drying process, e.g. in that the formation of covalent bonds, ionic interactions, etc. between the cell walls of two or more fixed cells is suppressed. By singularizing the cells, it is then possible to quantify individual cells in a flow-through cytometer.

In a preferred embodiment, the chemical homogenizing agent contains (a) a monosaccharide or a disaccharide, (b) a polyol, and (c) water. The monosaccharide, or disaccharide, respectively, can be of a natural or synthetic origin, wherein, in particular, a tetrose, pentose or hexose in the D-form or the L-form, e.g. erythrose, threose, ribose, arabinose, lyxose, xylose, allose, altrose, galactose, glucose, gulose, idose, mannose, talose and fructose can be used as a monosaccharide. As a disaccharide, in particular a compound selected from the group consisting of gentiobiose, isomaltose, lactose, lactulose, maltose, maltulose, raffinose, sucrose and trehalose can be used, although the invention is not limited to the use of these substances. A monosaccharide or disaccharide selected from the group consisting of fructose, galactose, glucose and sucrose is more preferred, and most preferred is glucose.

A polyol then serves as a further component of the chemical homogenizing agent used according to the invention, wherein the term, "polyol," as it is used in the present application, refers to a low molecular organic substance with at least two alcoholic hydroxy groups, and excludes the monosaccharides and disaccharides defined above. The polyol can be of natural or synthetic origin, and can be present in both the D-form and the L-form in the case of the presence of a stereo center or numerous stereo centers. Examples of polyols that are to be used according to the invention comprise ethylene glycol, glycerin, inositol, isomalt, mannitol, pentaerythritol, sorbitol and xylitol, but are not limited thereto. More preferably, a polyol is selected in the invention from the group consisting of ethylene glycol, glycerin, mannitol and sorbitol, wherein glycerin is most preferred.

As a third component, the chemical homogenizing agent then comprises water. The amount of water is normally set such that the amount of monosaccharide or disaccharide in the chemical homogenizing agent lies approx. in the range of 10%-70% by weight, preferably approx. 20%-60% by weight, more preferably approx. 30%-50% by weight, and most preferably approx. 35%-45% by weight, based on the overall weight of the chemical homogenizing agent. The amount of polyol in the chemical homogenizing agent normally lies in a range of approx. 5%-50% by weight, preferably approx. 10%-40% by weight, more preferably approx. 10%-30% by weight, and most preferably approx. 15%-25% by weight, based on the overall weight of the chemical homogenizing agent.

After the fixed cells have been homogenized by the homogenizing agent, the cells are dried appropriately, e.g. in a kiln or drying cabinet at a temperature in the range of 40° to 90° C., preferably at a temperature in the range of 60° to 80° C. The dried cells acquired in this manner are subsequently brought in contact with a detection reagent specific for the respective microorganism that is to be detected. In detail, the dried cells are typically placed in a suitable reaction vessel for this, and then a solution of a least one fluorescent-marked nucleic acid probe that is specific for the microorganism, i.e. a nucleic acid probe marked with a fluorescent dye, is first added thereto, in order to obtain a first reaction mixture. This first reaction mixture is then incubated in suitable conditions in order to obtain a bonding of the at least one fluorescence-marked nucleic acid probe to the corresponding target nucleic acid sequence in the cells of the microorganism that is to be detected.

After this step, the first reaction mixture is brought in contact with a solution of at least one quencher-marked nucleic acid probe, i.e. a nucleic acid probe marked with a quencher that at least partially quenches the fluorescence of the fluorescent dye in the fluorescent-marked nucleic acid probe, in order to obtain a second reaction mixture, wherein the quencher-marked nucleic acid probe has a nucleic acid sequence that is substantially complementary, and is preferably a reversed complement, to the nucleic acid sequence in the fluorescence-marked nucleic acid probe. The second reaction mixture is then incubated under suitable conditions as well, in order to obtain a bonding of the molecules of the fluorescence-marked nucleic acid probe not bonded to the target nucleic acid sequence to the quencher-marked nucleic acid probe and thus to at least partially quench the fluorescence of optionally free fluorescence-marked nucleic acid probes.

This means that in the method in the present invention, the solution of the at least one quencher-marked nucleic acid probe is added directly to the solution of the at least one fluorescence-marked nucleic acid probe, by means of which a previous separation of optionally excess fluorescence-marked nucleic acid probes by means of a rinsing step can be eliminated. Furthermore, only those fluorescence-marked nucleic acid probes that are bonded to the target nucleic acid sequence (i.e. in the cells of the microorganism that is to be specifically detected), contribute to the fluorescence signal. On the other hand, the signal of the free fluorescence-marked nucleic acid probes is substantially quenched by the hybridization with the quencher-marked nucleic acid probe. This reaction mechanism enables a single-step testing system.

As regards the proportion of the two nucleic acid probes, i.e. of the fluorescence-marked nucleic acid probe and the quencher-marked nucleic acid probe, the proportion depends on the conditions of the concrete embodiment of the method according to the invention, and can be easily determined by a person skilled in the art by means of routine tests. The required quenching of the fluorescence in the excess fluorescence-marked nucleic acid probes not bonded to the target nucleic acid sequence by the quencher-marked nucleic acid probes, however, implies that the proportions of quencher-marked nucleic acid probes to fluorescence-marked nucleic acid probes is at least 1:1, and preferably stipulates an excess of quencher-marked nucleic acid probes.

Regarding the incubation conditions for the first and second reaction mixtures, the incubation times and incubation temperatures can be determined by a person skilled in the field of microbial analysis based on the length and the GC content of the nucleic acid sequences and checked in a simple optimization process. The incubation time for the first reaction mixture obtained after adding the solution of the fluorescence-marked nucleic acid probes to the dried cells, however, is preferably approx. 60 to 120 minutes, and particularly preferably approx. 80 to 100 minutes, while the incubation temperature is preferably approx. 30° to 50° C., and particularly preferably approx. 40° C. The incubation time for the second reaction mixture obtained after adding the solution of the quencher-marked nucleic acid probes to the first reaction mixture is preferably approx. 5 to 30 minutes, and particularly preferably approx. 10 to 20 minutes, while the incubation temperature, again, is preferably approx. 30° to 50° C., and particularly preferably approx. 40° C.

FIG. 1 schematically illustrates the reactions in the method that is the basis for the invention, wherein both the fluorescence-marked nucleic acid probes as well as the quencher-marked nucleic acid probes are present in the concrete example as single-stranded DNA molecules. In detail, the fluorescence-marked nucleic acid probes, after they have been added to the appropriately fixed and dried cells, diffuse towards their target sequence and bond thereto. An rRNA functions here as the target molecule in the cells of the microorganism that is to be detected, wherein the sequence of the rRNA targeted by the fluorescence-marked nucleic acid probes is specific for the microorganism that is to be detected.

In contrast to the classic FISH technique in which they must be removed in a stringent rinsing step, un-bonded (i.e. excess) fluorescence-marked nucleic acid probes are captured by adding the quencher-marked nucleic acid probes, wherein a no longer fluorescent nucleic acid hybrid composed of fluorescence-marked nucleic acid probes and quencher-marked nucleic acid probes is formed. If a fluorescence-marked nucleic acid probe first bonds to a suitable target nucleic acid sequence, this fluorescence-marked nucleic acid probe will no longer hybridize with the quencher-marked nucleic acid probe.

Consequently, in cases in which the fluorescence-marked nucleic acid probes have bonded to the target nucleic acid sequence in the microorganism that is to be detected, a fluorescence is observed after excitation of the fluorescent dye in the fluorescence-marked nucleic acid probes, while in cases in which the fluorescence-marked nucleic acid probes are not bonded to the target nucleic acid sequence, no fluorescence is emitted as a result of the hybridization of the fluorescence-marked nucleic acid probes with the quencher-marked nucleic acid probes. As a result, the fluorescence of a particle detected in a flow-through cytometer is a direct qualitative and quantifiable signal for the microorganism for which the fluorescence-marked nucleic acid probe is specific.

In the foregoing, the method according to the invention was explained on the basis of nucleic acid probes that are composed of deoxyribonucleotides and can therefore also be referred to as DNA probes. It is understood, however, that other nucleic acid probes can also be used as long as these nucleic acid probes display the behavior described above with respect to the formation of hybrids in the microorganism that is to be detected.

In the present invention, the fluorescence-marked nucleic acid probes and/or the quencher-marked nucleic acid probes are preferably single-stranded nucleic acid probes. It is however also possible in the present invention that these nucleic acid probes, individually and independently of each other, are double-stranded. In cases in which at least one of the nucleic acid probes is double-stranded, it is preferred that only a part of the sequence of the fluorescence-marked nucleic acid probes, or a part of the sequence of the quencher-marked nucleic acid probes are double-stranded. The extent of formation of a double strand in the respective probes depends on the requirements for the hybridization with the target nucleic acid sequence and in particular the hybridization with the respective complementary probes.

Each one of the nucleic acid probes that is to be used in the present invention, and in particular the fluorescence-marked nucleic acid probe, is preferably formed as a DNA probe, RNA probe, PNA probe, or LNA probe, or as a combination of two or more thereof. The design or selection of the nucleotides that form the respective nucleic acid probes is within the scope of knowledge of the person skilled in the field of the invention, and can take place through routine procedures and considerations in light of the disclosure given herein, and in particular the presumed mechanism underlying the present invention.

As described above, the fluorescence-marked nucleic acid probe is specific for the microorganism that is to be detected. The generation of such nucleic acid probes is known to a person skilled in the field of microbial analysis, and is also described in greater detail in DE 10 2010 012 421 A1. The specificity is preferably determined via the degree of homology between the nucleic acid probe and its target nucleic acid sequence. The degree of homology is preferably at least 70%, more preferably at least 80%, even more preferably at least 95%, and most preferably at least 96%, 97%, 98%, 99%, or 100%. In one embodiment, the nucleic acid probe is substantially identical to the target nucleic acid sequence within the predefined homology values.

Alternatively, the nucleic acid sequence of the fluorescence-marked nucleic acid probe can be substantially reverse complementary to the target nucleic acid sequence. The above homology values then also apply as the degree of identity or complementarity for the nucleotide sequence of the nucleic acid probe with or to the target nucleic acid sequence. Alternatively, particularly in the case of a reverse complementary sequence, the degree of homology can also be defined by the conditions under which hybridization of the nucleic acid probe and the target sequence still takes place. The fluorescence-marked nucleic acid probe is preferably reverse complementary to the target sequence, in particular when it is hybridized with the target nucleic acid sequence under moderate or stringent conditions. These conditions are described by way of example in WO 00/68421 A1.

That stated herein with regard to the fluorescence-marked nucleic acid probe also applies substantially to the quencher-marked nucleic acid probe, wherein it is clear to the person skilled in the art that the quencher-marked nucleic acid probe is substantially reverse complementary to the fluorescence-marked nucleic acid probe and that the degree of complementarity between the quencher-marked nucleic acid probe and the fluorescence-marked nucleic acid probe can be defined in the same manner as the degree of complementarity between the target nucleic acid sequence in the microorganism that is to be detected and the fluorescence-marked nucleic acid probe.

Target nucleic acid sequences that allow for the specific detection of a microorganism are known in the field, wherein reference is made by way of example to the publications by Clementino et al. (J. Appl. Microbiol. 103 (2007), 141-151), Ni et al. (FEMS Microbiol. Lett. 270 (2007), 58-66), Leaw et al. (J. Clin. Microbiol. 45 (2007), 2220-2229) and Bhardwaj et al. (J. Med. Microbiol. 56 (2007), 185-189). Preferred target nucleic acid sequences are, in particular in this context, 16S rRNA, 23S rRNA, 18S rRNA, tRNA, EF-Tu, mRNA 16S-23S rRNA spacer, and 23S-5S rRNA spacer, wherein 16S rRNA and 23S rRNA are particularly preferred.

The length of the fluorescence-marked nucleic acid probes and the quencher-marked nucleic acid probes is, independently of one another, approx. 15 to 31 nucleotides, preferably approx. 17 to 25 nucleotides, more preferably approx. 17 to 23 nucleotides, and most preferably 17 or 18 nucleotides. In a preferred embodiment, the fluorescence-marked nucleic acid probes and the quencher-marked nucleic acid probes are substantially the same length. With regard to the selection of the lengths of the two nucleic acid probes, reference is also made to the criteria specified in DE 10 2010 012 421 A1.

Both nucleic acid probes can comprise more nucleotides than necessary for forming the aforementioned lengths, wherein these additional nucleotides preferably do not contribute to or participate in the formation of a double stranded structure if the fluorescence-marked nucleic acid probe is base-paired with the quencher-marked nucleic acid probe, wherein the base-pairing is preferably a Watson-Crick base pairing, and a hybridized complex is formed. In one embodiment, the lengths of the two nucleic acid probes and the complementary region are the same.

A fluorescent dye, also referred to as fluorophore herein, is a molecule that absorbs or is energetically excited by light at a characteristic wavelength, ideally at its absorption maximum. This light (photon) is then emitted after a certain time, e.g. either as fluorescence or as vibrational energy (heat). The fluorophore then returns to the energetically more favorable, non-excited ground level state. A quencher (acceptor) is a molecule that absorbs energy from an excited fluorophore (donator or donor), thus quenching its fluorescence emission.

In general, the weakening or quenching of a fluorescent signal is referred to as fluorescence quenching. For an optimal quenching efficiency, a precise coordination of the fluorescent dye to the corresponding quencher is decisive (Marras et al., Methods in Molecular Biology 335 (2006), 3-16). In selecting a suitable pair of a fluorescent dye and a quencher, a distinction can be made between whether the observed quenching is basically a static or dynamic quenching. The positioning of the fluorescent dye and the quencher can take place depending on whether it is a static or dynamic quenching.

With a so-called static quenching, or contact quenching, respectively, a non-fluorescent complex is formed between the fluorophore and the quencher in the excited state. The donor and acceptor are spatially close to each other in a static quenching ($\leq 20$ Å). The molecules interact directly through a proton-coupled electron transfer by means of the formation of hydrogen bonds (Förster, Ann. Phys. 2 (1948), 55-75; Lakowicz, Principles of Fluorescence Spectroscopy, Kluwer Academic/Plenum Publishers, New York, 1999).

It is also possible, however, to use the method of dynamic quenching, the so-called FRET quenching (Fluorescence Resonance Energy Transfer). In this case, the excited fluorophore transfers its energy to the quencher and then returns to the base state without emitting radiation. The donor and acceptor are spatially distanced to one another at approx. 40 to 100 Å (corresponding to ca. 3 to 30 nucleotides within a double-stranded DNA). One prerequisite for FRET quenching is also that the fluorescence emission spectrum of the donor overlaps the absorption spectrum of the acceptor.

In order to obtain such a quenching, it is preferred according to the invention that the fluorescent dye in the fluorescence-marked nucleic acid probe is located at the 3' end or close to the 3' end of the fluorescence-marked nucleic acid probe, and the quencher in the quencher-marked nucleic acid probe is located at the 5' end or close to the 5' end of the quencher-marked nucleic acid probe. Alternatively, the fluorescent dye in the fluorescence-marked nucleic acid probe can also be located at the 5' end or close to the 5' end of the fluorescence-marked nucleic acid probe, while the quencher in the quencher-marked nucleic acid probe is located at the 3' or close to the 3' end of the quencher-marked nucleic acid probe. For further details, reference is made in this context to DE 10 2010 012 421 A1.

It is understood that the fluorescence emitted by the fluorescent dye in the fluorescence-marked nucleic acid probe does not necessarily have to be entirely quenched by the quencher in the quencher-marked nucleic acid probe. For the purposes of the present invention, it is sufficient if there is a significant difference in the signal that can be detected by a detector system (i.e. the flow-through cytometer) between a cell marked with the fluorescence-marked nucleic acid probe and derived from the microorganism that is to be detected and the hybridization complex composed of the fluorescence-marked nucleic acid probe and the quencher-marked nucleic acid probe. The degree of quenching is normally 10% to 90% in this case, and preferably at least 50%.

The fluorescent dyes used for producing the fluorescence-marked nucleic acid probes are in particular those used in the classic FISH technology. The fluorescent dye can be selected, e.g., from the group consisting of FAM, TAMRA, CY3, Alexa 350, Pacific Blue, Coumarin, Cy2, Alexa 488, TET, Alexa 532, HEX, Alexa 546, TMR, Cy3.5, Alexa 568, Texas red, Alexa 594, Alexa 633, Cy5, Cy5.5, Alexa 660, Alexa 680, ATTO 490LS, Rox and Vic. It is understood that there is no limitation whatsoever regarding the suitability of fluorescent dyes, with the exception of those for which there is simultaneously a quencher that at least partially quenches the fluorescence of the fluorescent dye.

With regard to the design or selection of the quencher, there are likewise no fundamental limitations. It is understood, however, that the selection of the fluorescent dye and the quencher must be such that a significant quenching of the fluorescent signal of the fluorescent dye after its excitation takes place either directly or indirectly. A sufficient quenching is defined in this case in that it is possible to distinguish between the quenched state and the unquenched state. In the present invention it is therefore possible for the quencher itself to be a fluorescent dye.

Some exemplary combinations of fluorescent dyes and quenchers are listed in the following table.

| Fluorescent Dye | Corresponding Quencher |
| --- | --- |
| FAM | Dabcyl, BHQ-1, TAMRA |
| TAMRA | BHQ-2 |
| CY3 | BHQ-2 |

Further suitable combinations of fluorescent dyes and quenchers are given in Marras et al. (Nucl. Acids Res. 30 (2002), e122), the disclosure of which is herewith explicitly incorporated by reference.

To increase the specificity of the method according to the invention, in addition to the fluorescence-marked nucleic acid probe and the quencher-marked nucleic acid probe, so-called competitor probes can be added to the reaction. The term, "competitor probe," as it is used in the present application, refers in particular to oligonucleotides that mask potentially occurring unintended bonds, i.e. in particular binding sites, of the nucleic acid probes, in particular of the fluorescence-marked nucleic acid probe, and exhibit a higher sequence similarity to a microorganism that is not to be detected than to the microorganism(s) that are to be detected.

By using competitor probes, it is possible to prevent the fluorescence-marked nucleic acid probe from bonding to the nucleic acid sequence of a microorganism that is not to be detected, and thus from causing false positive signals. The competitor probe is typically unmarked, and is preferably used prior to adding the fluorescence-marked nucleic acid probe and the quencher-marked nucleic acid probe. The competitor probe should be substantially complementary to a target nucleic acid sequence of one or more microorganisms that are not to be detected.

The competitor probes, as they can be used in the present invention, can be a DNA or RNA sequence, which normally contains between 12 and 100 nucleotides, preferably between 15 and 50 nucleotides, and particularly preferably between 17 and 25 nucleotides. By selecting a defined sequence, the hybridization of the fluorescence-marked nucleic acid probe or the quencher-marked nucleic acid probe to the nucleic acid sequence of a taxonomical unit or an artificially generated group of microorganisms can be blocked.

Complementarity to the nucleic acid sequence that is to be blocked should exist over 100% of the sequence in a competitor probe of 15 nucleotides. With competitor probes of more than 15 nucleotides, one or more mismatch sites are allowed, depending on the length. Such competitor probes are described, e.g., in the international patent application WO 2005/031004 A2, the disclosure of which is herewith explicitly incorporated by reference.

It is within the scope of the present invention that in addition to the pair composed of a fluorescence-marked nucleic acid probe and a quencher-marked nucleic acid probe (first nucleic acid probe pair), at least one further pair composed of a fluorescence-marked nucleic acid probe and a respective matching quencher-marked nucleic acid probe (second nucleic acid probe pair, third nucleic acid probe pair, etc.) can be used. Each further nucleic acid probe pair is designed in accordance with the first nucleic acid probe pair, wherein the fluorescence-marked nucleic acid probes of the second, third, etc. nucleic acid probe pairs each address a target nucleic acid sequence in the microorganism that is to be detected other than the fluorescence-marked nucleic acid probe of the first nucleic acid probe pair.

This means that in a preferred variation of the method according to the invention, numerous fluorescence-marked nucleic acid probes with different nucleic acid sequences, in each case specific for the microorganism that is to be detected, are first added in the form of a single solution or numerous solutions to the fixed and dried cells in step (d) in order to hybridize numerous fluorescence-marked nucleic acid probes on target nucleic acid sequences of the microorganism that is to be detected in parallel, and in step (f), a number of different quencher-marked nucleic acid probes corresponding to the number of fluorescence-marked nucleic acid probes are added in the form of a single solution or numerous solutions, in order to capture the different fluorescence-marked nucleic acid probes, and to thus at least partially quench their fluorescence.

In another embodiment of the method according to the invention, the sample that is to be analyzed contains more than one microorganism, i.e. at least two different microorganisms, which are to be detected in parallel. In this case, it is preferred that the fluorescence-marked nucleic acid probe in the second nucleic acid probe pair is specific for the second microorganism that is to be detected, the fluorescence-marked nucleic acid probe in the third nucleic acid probe pair is specific for the third microorganism that is to be detected, etc. As a matter of course, however, there is also the possibility of using, in the detection of each microorganism that is to be detected, in each case more than just one fluorescence-marked nucleic acid probe that is specific to the respective microorganism.

After the fluorescence of potential excess fluorescence-marked nucleic acid probe(s) has been at least partially quenched, the second reaction mixture for detecting the fluorescence emitted by the cells containing the fluorescence-marked nucleic acid probe(s) in the microorganism that is to be detected is placed in a conventional flow-through cytometer and analyzed therein. Because the second reaction mixture can be placed as such (i.e. without further processing and rinsing steps) into the flow-through cytometer, the work effort is reduced, and potential sample losses can be prevented. In this regard, the invention also relates to a flow-through cytometer for use in the method according to the invention.

The fluorescence emitted from the cells can be used directly for quantifying the number of cells, in particular whole cells, of the microorganism that is to be detected. The values obtained from this measurement are then visualized on the computer in the form of histograms or dot-plots, and allow for a reliable conclusion regarding the type and amount of the microorganisms contained in the sample. The method according to the invention thus allows for a direct detection as well as quantification of a microorganism or numerous microorganisms as whole cells in the framework of a whole cell hybridization.

Substantial advantages of the method according to the invention are thus the very simple execution, as well as speed, reproducibility, reliability, and objectivity, with which the specific detection of microorganisms in a sample is possible. Another advantage is that the advantageous method of in situ hybridization in the solution can be carried out in such a manner that any rinsing steps are dispensable. This simplifies the execution in the method, and thus reduces the time required for the preparation steps. Because the entire method can be carried out in a single reaction vessel, there are no losses when transferring to new reaction vessels, such that it is possible to obtain a more precise quantification.

The present invention shall now be explained in greater detail based on the following examples, comparison examples, and the drawings.

EXAMPLE 1

The method for specific detection of microorganisms is exemplified by the detection of *Alicyclobacillus* spec. in fruit juice beverages.

An orange juice concentrate sample that is to be examined was cultivated appropriately for at least 48 hours. 0.9 ml of the culture was subsequently transferred to a suitable reaction vessel, and 0.9 ml of a fixing agent containing 80% ethanol was added.

The fixed cells were sedimented through centrifuging (4,000×g, 5 min., room temperature), and 20 µl of a homogenizing agent were added, which homogenizing agent was obtained by mixing a 50% by weight aqueous glucose solution with glycerin in a weight ratio of 8:2, and subsequently dried for 20 minutes at 80° C. in a kiln.

35 µl of a hybridization solution are subsequently added to the dried and homogenized cells in a reaction vessel, in which 20 ng of a nucleic acid probe specific for *Alicyclobacillus* spec. and marked with FAM as the fluorescent dye were dissolved in an aqueous buffer (solution of 0.9 M NaCl and 0.02 M tris-HCl (pH 8.0) in a mixture of 65% water by weight and 35% formamide by weight). The fluorescence-marked nucleic acid probe had a length of 20 nucleotides and had a 100% degree of homology to the target nucleic acid sequence.

After the reaction mixture obtained in this manner was incubated for 1.5 hours at 40° C., 35 µl of a quencher solution were added to the reaction mixture, in which quencher solution 20 ng of a nucleic acid probe marked with BHQ1 as the quencher were dissolved in an aqueous buffer (solution of 0.14 M NaCl and 0.04 M tris-HCl (pH 8.0) in water). The quencher-marked nucleic acid probe had a length of 20 nucleotides and a 100% degree of homology to the nucleic acid sequence of the fluorescence-marked nucleic acid probe.

The reaction mixture obtained in this manner was incubated for a further 15 minutes at 40° C. and then placed without further processing in a flow-through cytometer (model CyFlow® Cube6 from Sysmex Deutschland GmbH), and analyzed and evaluated therein at a flow-through speed of 0.5 µl/second.

Figure 2:
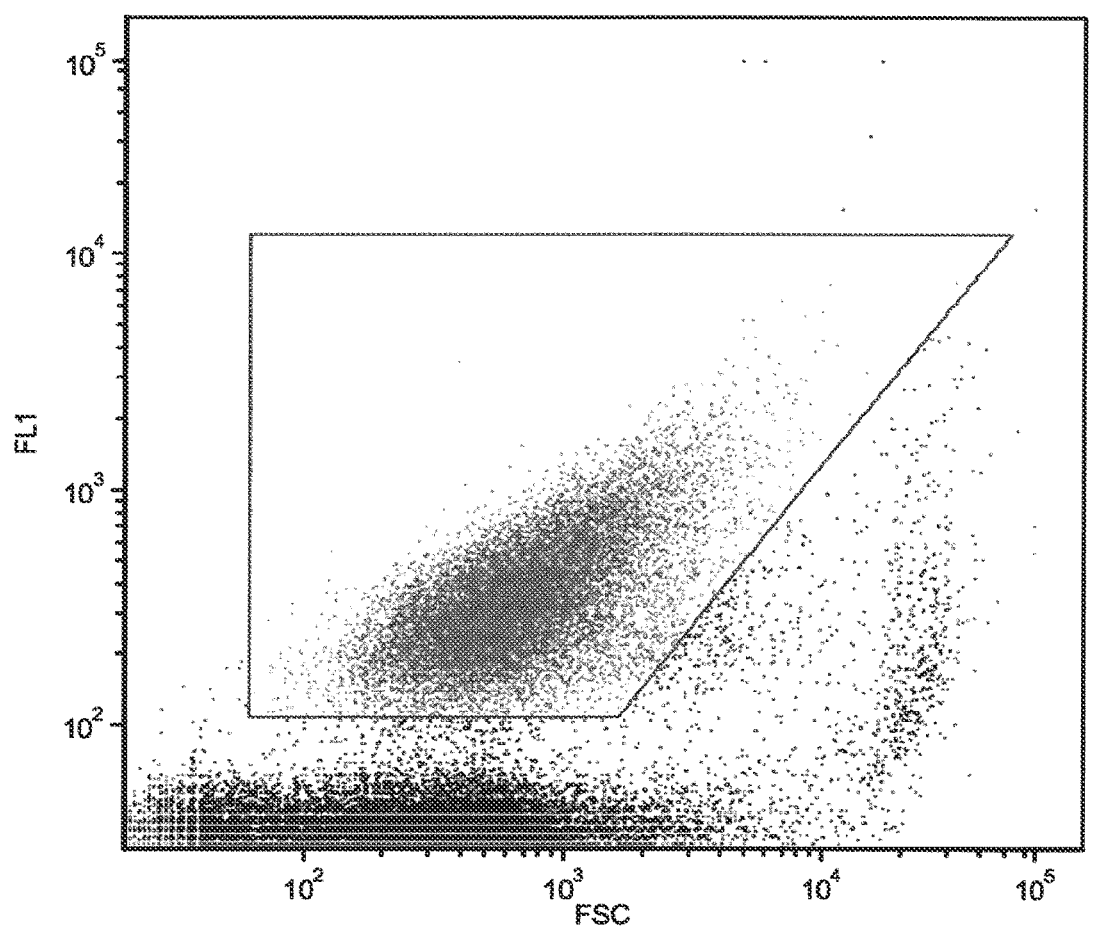
FIG. 2 shows the results of a measurement of the fluorescent signal of the cells is plotted in the dot-plot diagram along the y-axis over the dispersion along the x-axis, which is a measure for the size of the particle.

FIG. 2 shows the results of the measurement. The fluorescent signal of the cells is plotted in the dot-plot diagram along the y-axis over the dispersion along the x-axis, which is a measure for the size of the particle.

COMPARISON EXAMPLE 1

Figure 3:
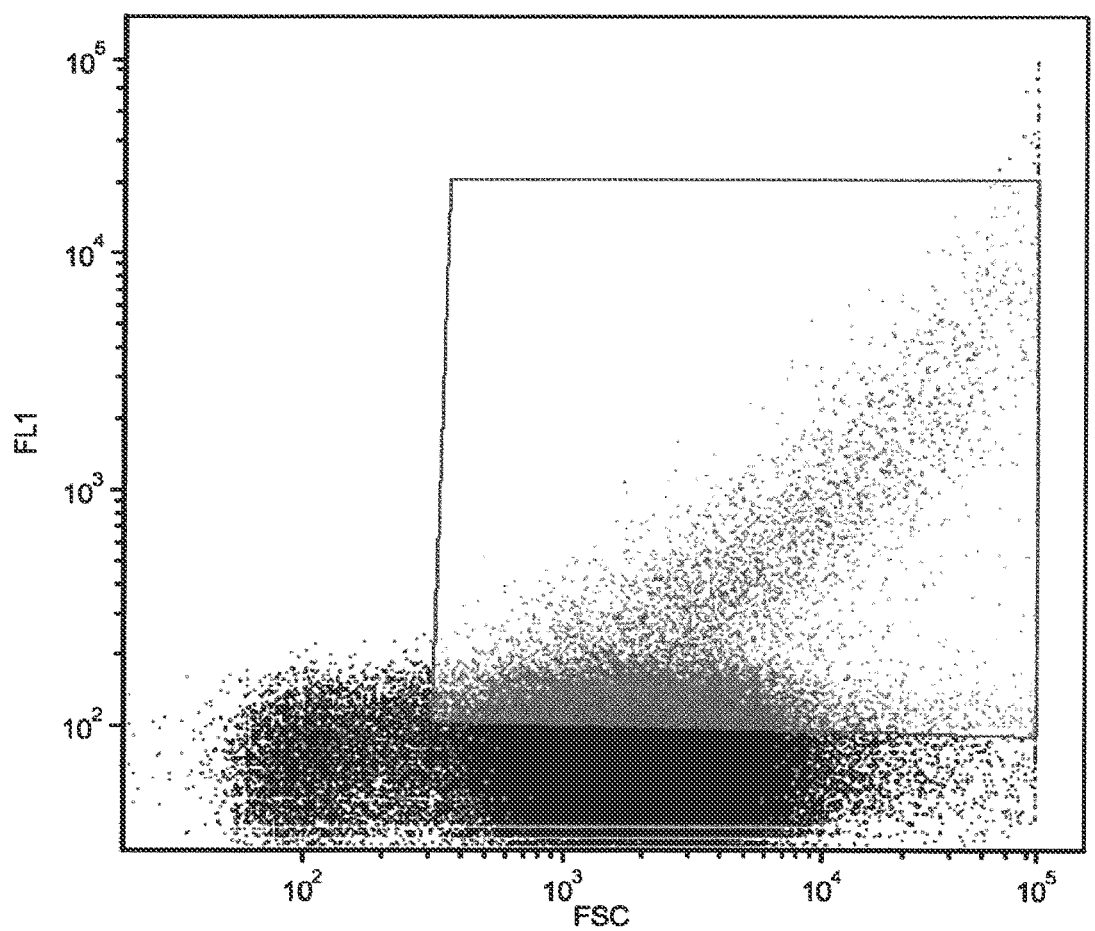
FIG. 3 illustrates the results of a measurement of FIG. 2 with the exception that prior to drying the fixed cells, no homogenizing agent was added.

Example 1, described above, was repeated, with the exception that prior to drying the fixed cells, no homogenizing agent was added. The results are shown in FIG. 3.

Because of the absence of the homogenizing agent, only a few, but very large particles were detected, each of which comprised clusters of different numbers of coherent individual cells. Because of the cluster formation, a quantification of the number of cells based on the number of particles detected in the flow-through cytometer was no longer possible.

A further disadvantage of the cluster formation results from the strongly dispersed distribution of the detected particles in relation to the size (x-axis of the dot-plot) and the intensity of the detected fluorescent signal (y-axis of the dot-plot), because a cluster formed by a large number of individual cells is seen by the detector as a particle with a higher intensity of the fluorescent signal than a cluster consisting of a lower number of individual cells. Accordingly, the distribution of the detected particles is dispersed to a large extent in the dot-plot, which strongly limits a differentiated determination of the organisms.

COMPARISON EXAMPLE 2

Figure 4:
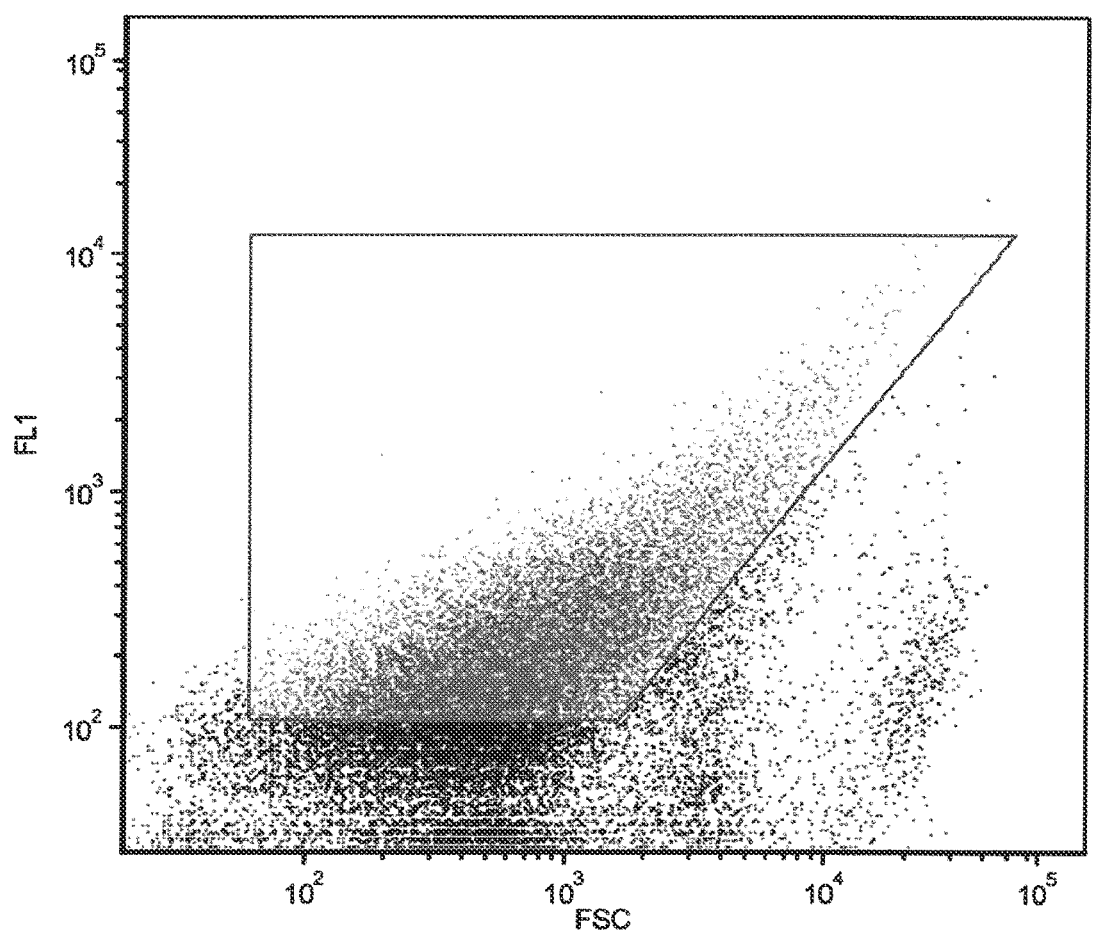
FIG. 4 illustrates the results of a measurement of FIG. 2 with the exception that the method described in WO 03/083131 A1 was employed, and no quencher-marked nucleic acid probe was used.

Example 1, described above, is substantially repeated, with the exception that the method described in WO 03/083131 A1 was employed, and no quencher-marked nucleic acid probe was used. The result is shown in FIG. 4.

Because of the absence of the quencher, the fluorescence of the unbounded fluorescence-marked nucleic acid probes was not quenched. The rest of the unbounded fluorescence-marked nucleic acid probes that could not be entirely removed by rinsing, contributed to an increase in the background noise in the measurement and resulted in a poorer separation of the fluorescence signal from the background noise.

EXAMPLE 2

Figure 5:
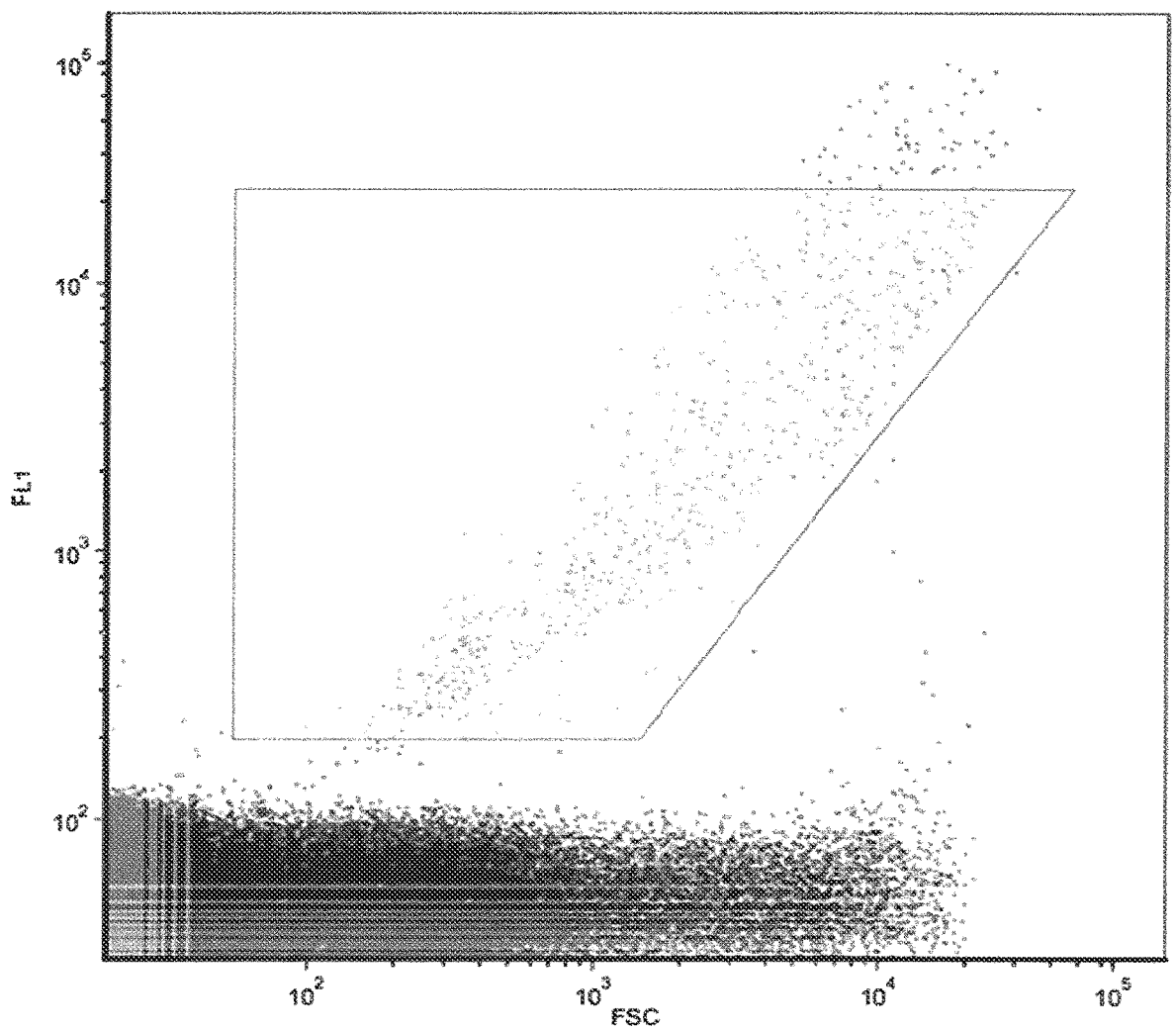
FIG. 5 illustrates the results of a measurement of FIG. 2 with the exception that instead of the homogenizing agent used in Example 1, 70% ethanol was used as the homogenizing agent.

Example 1, described above, was repeated, with the exception that instead of the homogenizing agent used in Example 1, 70% ethanol was used as the homogenizing agent. The results are shown in FIG. 5.

Because of the use of 70% ethanol as the homogenizing agent, a clear improvement of the distribution of the detected particles was obtained in comparison with the Comparison Example 1, in which no homogenizing agent was added prior to drying the fixed cells.

As can be seen based on a relatively high number of large particles with intense fluorescence signals, however, clusters were still formed with the use of 70% ethanol as the homogenizing agent, which clusters consisted of numerous coherent individual cells.

The invention claimed is:

1. A method for detecting a microorganism in a sample, comprising the steps:
   (a) obtaining the sample;
   (b) fixing the cells contained in the sample in place with a fixing agent, and separating the fixed cells obtained thereby from the sample, in order to obtain fixed cells;
   (c) bringing the fixed cells in contact with a chemical homogenizing agent and drying the homogenized cells obtained thereby, in order to obtain dried cells;
   (d) bringing the dried cells in contact with a solution of a fluorescence marked nucleic acid probe specific for the microorganism that is to be detected, in order to obtain a first reaction mixture;
   (e) incubating the first reaction mixture in order to bond the fluorescence marked nucleic acid probe to the corresponding target nucleic acid sequence in the cells of the microorganism that is to be detected;
   (f) bringing the first reaction mixture in contact with a solution of a quencher-marked nucleic acid probe, in order to obtain a second reaction mixture, wherein the quencher-marked nucleic acid probe comprises a quencher that at least partially quenches the fluorescence of the fluorescence-marked nucleic acid probe, and contains a nucleic acid sequence that is substantially complementary to the nucleic acid sequence of the fluorescence-marked nucleic acid probe;
   (g) incubating the second reaction mixture to cause a bonding of the molecules of the fluorescence-marked nucleic acid probe not bonded to the target nucleic acid sequence in the cells of the microorganism that is to be detected to the quencher-marked nucleic acid probe; and
   (h) placing the second reaction mixture in a flow-through cytometer, and detecting the fluorescence emitted from the cells of the microorganism that is to be detected containing the fluorescence-marked nucleic acid probe;
   wherein the chemical homogenizing agent comprises (a) one of a monosaccharide and disaccharide, (b) a polyol, and (c) water.

2. The method according to claim 1, wherein the sample is a liquid sample.

3. The method according to claim 1, wherein the microorganism is a bacteria, a fungi, or a single-cell higher organism (protozoa).

4. The method according to claim 3, wherein the bacteria is a bacteria from the genus *Acinetobacter, Alicyclobacillus, Aquabacteria, Arcobacter, Bacillus, Campylobacter, Enterobacteriaceae, Escherichia, Lactobacillus, Lactococcus, Legionella, Listeria, Microthrix, Nitrobacter, Nitrosococcus, Nitrosomonas, Nitrospira, Nitrotoga, Porpionibacteria, Salmonella, Shigella*, or *Streptococcus*.

5. The method according to claim 3, wherein the fungi is a fungi from the genus *Aspergillus, Candida, Debaromyces, Dekkera, Penicillium, Pichia* or *Saccharomyces*.

6. The method according to claim 1, wherein the one of a monosaccharide and disaccharide is a substance selected from the group consisting of fructose, galactose, glucose and sucrose.

7. The method according to claim 1, wherein the polyol is a substance selected from the group consisting of ethylene glycol, glycerin, mannitol and sorbitol.

8. The method according to claim 1, wherein the target nucleic acid sequence in the cells of the microorganism that is to be detected is selected from the group comprising 16S rRNA, 23S rRNA, 18S rRNA, tRNA, EF-Tu, mRNA 16S-23S rRNA spacer, and 23S-5S rRNA spacer.

9. The method according to claim 1, wherein the fluorescence-marked nucleic acid probe is one of (i) substantially identical and (ii) substantially reverse complementary to the target nucleic acid sequence in the cells of the microorganism that is to be detected.

10. The method according to claim 1, wherein the fluorescence-marked nucleic acid probe is selected from a fluorescence-marked DNA probe, RNA probe, PNA probe, and LNA probe.

11. The method according to claim 1, wherein the fluorescent dye of the fluorescence-marked nucleic acid probe is located at the 3' end or close to the 3' end of the fluorescence-marked nucleic acid probe, and the quencher of the quencher-marked nucleic acid probe is located at the 5' end or close to the 5' end of the quencher-marked nucleic acid probe.

12. The method according to claim 1, wherein numerous fluorescence-marked nucleic acid probes with different nucleic acid sequences specific for the respective microorganism that is to be detected are added in step (d), and in step (f), a number of different quencher-marked nucleic acid probes corresponding to the number of fluorescence-marked nucleic acid probes are added.

13. The method according to claim 1, wherein the sample contains more than one microorganism, and numerous different microorganisms are detected simultaneously.

14. A flow-through cytometer for use in the method according to claim 1.

15. The method according to claim 1, wherein the fluorescent dye of the fluorescence-marked nucleic acid probe is located at the 5' end or close to the 5' end of the fluorescence-marked nucleic acid probe, and the quencher of the quencher-marked nucleic acid probe is located at the 3' end or close to the 3' end of the quencher-marked nucleic acid probe.

16. A method for detecting a microorganism in a sample, comprising the steps:
   (a) obtaining the sample;
   (b) fixing the cells contained in the sample in place with a fixing agent, and separating the fixed cells obtained thereby from the sample, in order to obtain fixed cells;
   (c) bringing the fixed cells in contact with a chemical homogenizing agent and drying the homogenized cells obtained thereby, in order to obtain dried cells;
   (d) bringing the dried cells in contact with a solution of a fluorescence-marked nucleic acid probe specific for the microorganism that is to be detected, in order to obtain a first reaction mixture;
   (e) incubating the first reaction mixture in order to bond the fluorescence marked nucleic acid probe to the corresponding target nucleic acid sequence in the cells of the microorganism that is to be detected;
   (f) bringing the first reaction mixture in contact with a solution of a quencher-marked nucleic acid probe in order to obtain a second reaction mixture;
   (g) incubating the second reaction mixture to cause a bonding of the molecules of the fluorescence-marked nucleic acid probe not bonded to the target nucleic acid sequence in the cells of the microorganism that is to be detected to the quencher-marked nucleic acid probe; and
   (h) placing the second reaction mixture in a flow-through cytometer and detecting the fluorescence emitted from the cells of the microorganism that is to be detected containing the fluorescence-marked nucleic acid probe;
   wherein the chemical homogenizing agent comprises (a) one of a monosaccharide and disaccharide, (b) a polyol, and (c) water.

17. The method according to claim 16, wherein the one of a monosaccharide and disaccharide is a substance selected from the group consisting of fructose, galactose, glucose and sucrose.

18. The method according to claim 16, wherein the polyol is a substance selected from the group consisting of ethylene glycol, glycerin, mannitol and sorbitol.

19. A method of using a flow-through cytometer in the detection method according to claim 16.

* * * * *